United States Patent [19]

Kastrubin

[11] 4,334,525
[45] Jun. 15, 1982

[54] METHOD OF AFFECTING CENTRAL NERVOUS SYSTEM BY PULSE CURRENTS

[76] Inventor: Eduard M. Kastrubin, Frunzenskaya naberezhnaya, 36, kv. 105, Moscow, U.S.S.R.

[21] Appl. No.: 205,982

[22] Filed: Nov. 12, 1980

[51] Int. Cl.³ .............................................. A61N 1/34
[52] U.S. Cl. .................................................. 128/1 C
[58] Field of Search ........... 128/1 C, 731, 732, 420 A, 128/420 R, 791, 792

[56] References Cited

U.S. PATENT DOCUMENTS 3,762,396 10/1973 Ballentine et al. ................... 128/1 C
3,989,051 11/1976 Nozhnikov et al. .................. 128/1 C
4,121,593 10/1978 Kastrubin et al. .................... 128/1 C

FOREIGN PATENT DOCUMENTS 467502 6/1937 United Kingdom ........... 128/420 A
312609 8/1975 U.S.S.R. .

OTHER PUBLICATIONS

"Zdorovye", USSR, No. 11, 1976, p. 9, *Two Hemispheres—One Brain*, L. A. Kukuev, D.M.
V. V. Ivanov, "Asymmetry of the brain and symbolic systems", Soviet Radio, Moscow, 1978, pp. 83, 107, 157.

*Primary Examiner*—William E. Kamm
*Attorney, Agent, or Firm*—Fleit & Jacobson

[57] ABSTRACT

A method of affecting the central nervous system by pulse currents, wherein the region of the forehead and the neck under the mastoid processes is affected by a combination of pulse current and an additional d-c component. Current is initially applied to the left hemisphere whereupon the right hemisphere is affected simultaneously and separately at the moment complex resistance of the left hemisphere decreases. The mean current in the region of the right hemisphere is constantly maintained higher than the mean current in the left hemisphere.

4 Claims, 1 Drawing Figure

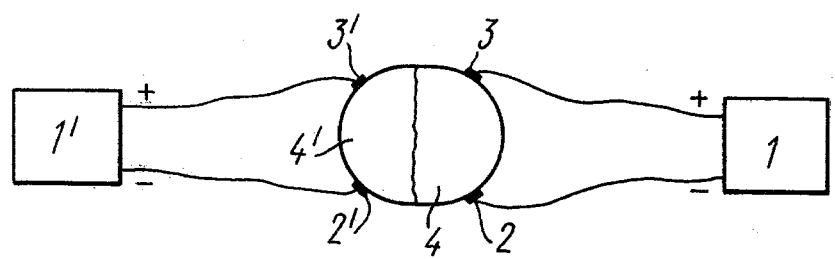

METHOD OF AFFECTING CENTRAL NERVOUS SYSTEM BY PULSE CURRENTS

The present invention relates to medicine and in particular to a method of affecting the central nervous system by pulse currents. More specifically, it may be used to advantage in obstetrics and gynecology.

Known in the art is a method of affecting the central nervous system by square pulse currents in conjunction with an additional d-c galvanic component, which are applied by the use of electrodes arranged in the region of the forehead (cathode) and in the region of the neck under the mastoid processes (anode), said method being commonly known as the central electroanalgesia method (cf. USSR Inventor's Certificate No. 312,609 filed Sept. 16, 1969 and published in 1974). A disadvantage of the aforesaid method is that it generally fails to consider the functional asymmetry of the cerebral hemispheres, which is an essential feature of the human central nervous system.

In the above method no account is taken of the fact that the right cerebral hemisphere ensures well-defined emotionally coloured sensations (cf. "Zdorovye", USSR, No. 11, 1976, p. 9, in Russian) and contains a musical centre which may be affected for curative and anesthetic purposes in modern medicine.

Moreover, the right cerebral hemisphere provides a possibility of isolation from external stimuli, contributes to the creation of hypnotic states and acts as an "emotion regulator" (cf. V. V. Ivanov "Asymmetry of the brain and symbolic systems", "Soviet Radio", Moscow, 1978, pp. 83, 107, 157, in Russian). The use of central electroanalgesia with no account taken of the functional peculiarities of the central nervous system may in certain instances excessively increase the number of pulse-treatment procedures before parturition or during the act of delivery for regulating the labour activity.

The curative and anesthetic effect may be achieved more rapidly and in a more profound manner only when the mean current in the patient's circuit is set to a maximum value at which the sensation threshold may be exceeded, a disadvantage causing unpleasant sensations at the points where the electrodes are applied.

It is an object of the present invention to provide a method of affecting the patient's central nervous system by pulse currents, which permits achieving a desired effect in a more rapid manner without exceeding the patient's sensation threshold at the points where electrodes are applied.

Another object of the invention is to provide a method of affecting the central nervous system at which the structural and functional peculiarities of the human cerebral hemispheres are accounted for in the most complete manner possible.

The foregoing and other objects of the invention are accomplished by that a pulse effect is first produced in the region of the left hemisphere whereupon the right hemisphere is affected simultaneously at the moment the complex resistance of the left hemisphere decreases. The mean current in the patient's circuit comprising the right hemisphere exceeds the mean current obtained in the left hemisphere at the moment the complex resistance under the electrodes changed.

To expedite the treatment effect without causing any adverse reactions under the electrodes, the amount of pulse effect is regulated by increasing the mean current at the initial stage only in the region of the right hemisphere considering that the mean current in the region of the left hemisphere will subsequently be decreased. The ratio of the mean current in the region of the right hemisphere to that in the region of the left hemisphere should be 2:1 so that only the sum current equals the maximum current value in the patient's circuit with the prior art treatment methods. The 2:1 current ratio allows sharply reducing such output pulse-treatment parameters as frequency, amplitude and duration in each hemisphere, another advantage being the possibility of eliminating adverse reactions when expediting the central electroanalgesia effect and increasing the amount of pulse effect.

The effectiveness of the hereinproposed treatment method is enhanced owing to the fact that the amount of pulse effect is regulated by deepening cathodic depression mainly in the region of the right cerebral hemisphere which acts as an "emotion regulator", determines the external stimulus perception intensity and is functionally interrelated to those areas of the central nervous system which define the reaction of an individual to painful sensations.

The invention will now be described further with reference to specific embodiments thereof and the drawing enclosed showing schematically the apparatus for carrying out the inventive method.

The method forming the subject of the present invention may be accomplished by the use of current sources furnishing regulated voltage pulses and including means for continuously adjusting the pulse recurrence rate and duration with constant and variable on-off ratios, say, by the use of the apparatus according to U.S. Pat. No. 4,185,640 granted to Kostrubin et al. on Jan. 1, 1980. No detailed description of the apparatus is given herein since it is mentioned for reference only. Two such apparatuses I and I', each comprising two electrodes (a cathode and an anode), will be needed to accomplish the method in compliance with the present invention. The cathode 3 and anode 2 of one apparatus I are applied to the right hemisphere 4, while the cathode 3' and anode 2' of the other are applied to the left hemisphere 4'.

For brevity the cathode 3 and anode 2 applied to the right hemisphere 4 will hereinafter be referred to as a first pair of electrodes and the cathode 3' and anode 2' applied to the left hemisphere 4 as a second pair of electrodes. On application, the first pair of electrodes is connected to one apparatus according to U.S. Pat. No. 4,185,640 and the second pair of electrodes to a similar apparatus.

The operating procedure is as follows. Power is applied to both apparatuses. Then the pulse recurrence rate is adjusted for approximately 150 to 200 Hz in both apparatuses and the pulse duration for 0.1 to 0.2 ms.

Next, the mean current is increased to 0.1–0.2 mA observing a milliammeter by regulating an additional d-c component in the apparatus wherein the first pair of electrodes is connected to the left hemisphere. The pulse recurrence rate is then increased to 500 Hz as indications are obtained in the region where the electrodes are applied. Thereafter the output voltage is increased until the mean current in the patient's circuit reaches 0.5–0.6 mA. When unpleasant sensations appear under the electrodes, the pulse recurrence rate is increased to 800–1000 Hz and the additional d-c component is eliminated within 10–20 min. The left hemisphere is continuously affected for some 15 to 20 min, even slight deflections of the meter pointer to the right may indicate that the complex resistance under the electrodes has decreased.

Then the output voltage of the second apparatus connected to the right hemisphere is increased simultaneously and separately and the mean current in the patient's circuit is set to 0.8 mA in the above manner.

Before parturition, currents of 0.4 mA and 0.8 mA are recommended for the left and right cerebral hemispheres, respectively.

For labour anesthesia and regulation, the recommended currents are 0.5 or 0.6 mA for the left hemisphere and 1.0 mA or 1.2 mA for the right hemisphere.

In the case of one pregnant woman before parturation a diffusive regular alpha rhythm was observed on application of pulses after the first treatment procedure with background electrical activity of brain. Intensifying the inhibition processes has led to labour activity after 2 or 3 treatment procedures.

In instances when the organism of a pregnant person is biologically prepared for the act of delivery, the pulse effect causes the appearance of labour activity after 1 or 2 treatment procedures, said activity being subsequently accompanied by increased cerebral cortex stimulation due to birth pains.

The pulse effect in compliance with the hereinproposed method will intensify the inhibition processes in the case when the organism of a pregnant person is not biologically prepared for the act of delivery.

An example of enhanced treatment effectiveness without exceeding the patient's sensation threshold under the electrodes is the case of a woman pregnant over 39-40 weeks, who was facing first spontaneous partus occipital delivery.

Before pulse treatment in compliance with the hereinproposed method the labour activity has continued for 8 h 40 min. The birth pains have been weak lasting for 20 to 25 s every 7 or 8 min, and the neck of the uterus has been opened 3 cm wide.

After the pulse treatment for 1 h 40 min according to the method forming the subject of the present invention the birth pains have grown stronger lasting for 30 to 35 s every 4 min, and the neck of the uterus has been opened 5 to 6 cm wide.

There has been another treatment procedure for 1 h 30 min after a short interval to record the electrical activity of the brain.

The neck of the uterus has then been fully opened.

The time elapsed from the development of labours to the beginning of pulse effect has bern 3 h 50 min. The total hemorrhage has been 150.0 mlit.

The total duration of the labour periods has been: 13 h 10 min (period one); 35 min (period two: and 10 min (period III). The infant has been given 9.9 points by the upgar score. A single coil has been formed by the umbilical cord wound around the neck.

The labour has been completely painless and the inhibition process has been substantially deeper.

The mean current value has reached 0.5 mA in the left hemisphere and 1.0 mA in the right hemisphere. The painful sensations have decreased with an increase of the mean current in the region of the right hemisphere.

The woman in labour has not experienced any unpleasant sensations in the region where the electrodes have been applied. The sum treatment current has amounted to 1.5 mA.

The use of the hereinproposed method allows sharply increasing the regulation effect in pulse treatment by taking into account the physiological peculiarities of the central nervous system. In the method forming the subject of the present invention each cerebral hemisphere is affected by minimum current and output voltage. Adverse reactions are generally prevented and the entire treatment effect becomes more profound being accompanied by more intensive inhibition processes in the cerebral cortex. Thus, optimum conditions are provided for obtaining the desired functional state of the central nervous system.

What is claimed is:

1. A method of affecting the central nervous system by pulse currents consisting in that the region of the forehead and the neck under the mastoid processes is affected by a combination of pulse current and an additional d-c component, wherein, according to the invention, current is initially applied to the left hemisphere after which the right hemisphere is affected simultaneously and separately at the moment complex resistance of the left hemisphere decreases, the mean current in the region of the right hemisphere being constantly maintained greater than the mean current in the region of the left hemisphere.

2. A method as claimed in claim 1, wherein the mean current is varied by affecting the right hemisphere and the mean current in the region of the left hemisphere is set so that its value is constantly smaller than the mean current in the region of the right hemisphere.

3. A method as claimed in claim 1, wherein the mean current in the region of the right hemisphere is twice that in the region of the left hemisphere.

4. A method as claimed in claim 1, wherein the right hemisphere is affected 15 to 20 min after the initial effect upon the left hemisphere.

* * * * *